United States Patent [19]
Sasaki et al.

[11] 3,949,023
[45] Apr. 6, 1976

[54] NOVEL OXIMINO-PHOSPHOROTHIOLATE DERIVATIVES

[75] Inventors: Mitsuru Sasaki; Isao Ohno, both of Minoo; Hisami Takeda, Takarazuka; Takeo Satomi; Kunio Mukai, both of Amagasaki, all of Japan

[73] Assignee: Sumitomo Chemical Co., Ltd., Osaka, Japan

[22] Filed: Dec. 6, 1973

[21] Appl. No.: 422,388

[30] Foreign Application Priority Data
Dec. 8, 1972    Japan.............................. 47-123592

[52] U.S. Cl. ......... 260/944; 260/293.85; 260/340.5; 260/941; 260/943; 424/200; 424/203; 424/211
[51] Int. Cl.² ..................... C07F 9/165; A01N 9/36; C07D 317/14; C07D 211/08
[58] Field of Search ..................................... 260/944

[56] References Cited
UNITED STATES PATENTS 2,957,016  10/1960  Diamond ............................ 260/944
3,717,690  2/1973  Newman .......................... 260/944 X

*Primary Examiner*—Anton H. Sutto
*Attorney, Agent, or Firm*—Sughrue, Rothwell, Mion & Zinn

[57] ABSTRACT

Oximino-phosphorothiolate derivatives represented by the formula,

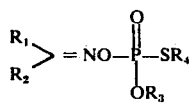

wherein $R_1$, $R_2$, $R_3$ and $R_4$ are as hereinafter defined, which are useful as a controlling agent for agricultural pests containing the oximino-phosphorothiolate derivatives as active ingredients, as well as processes for preparing the compounds and the composition are disclosed.

3 Claims, No Drawings

NOVEL OXIMINO-PHOSPHOROTHIOLATE DERIVATIVES

BACKGROUND OF THE INVENTION

Field of the Invention

The present invention relates to a controlling agent for agricultural pests characterized in that the controlling agent contains, as an active ingredient, a new oximino-phosphorothiolate of the formula (I),

wherein $R_1$ is an alkyl($C_1$-$C_4$) group; $R_2$ is an alkyl($C_1$-$C_4$), alkyl($C_1$-$C_4$)thioalkyl($C_1$-$C_4$), alkoxy($C_1$-$C_4$)(alkyl($C_1$-$C_4$)), cycloalkyl($C_3$-$C_6$), alkenyl($C_2$-$C_5$) or halogenated alkyl($C_1$-$C_4$) group; $R_1$ and $R_2$ may be joined together via a —$(CH_2)_k$— linkage, in which $k$ is an integer of 4 to 5, to form a ring structure which may be substituted with a methyl group for a nucleus hydrogen; $R_3$ is an alkyl($C_1$-$C_4$) group; and $R_4$ is an alkyl($C_1$-$C_4$), alkenyl($C_2$-$C_5$), alkynyl($C_2$-$C_5$), alkyl($C_1$-$C_4$)-thioalkyl($C_1$-$C_4$), alkoxy($C_1$-$C_4$)alkyl($C_1$-$C_4$), halogenated alkenyl($C_2$-$C_5$), carbamoylmethyl of the formula,

(wherein $R_5$ is a hydrogen atom, or an alkyl($C_1$-$C_4$) or alkenyl($C_2$-$C_5$) group; $R_6$ is a hydrogen atom, or an alkyl($C_1$-$C_4$) or alkenyl($C_2$-$C_5$) group; and $R_5$ and $R_6$ may be joined together via a —$(CH_2)_l$— group, in which $l$ is an integer of 4 to 5, to form a ring structure which may be substituted with a methyl group for a nucleus hydrogen) alkoxycarbonylalkyl of the formula,

(in which $R_7$ is an alkyl($C_1$-$C_4$) group and $R_8$ is a hydrogen atom, or an alkyl($C_1$-$C_4$) or phenyl group) or a substituted or unsubstituted aralkyl group of the formula,

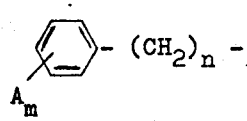

(in which A is a hydrogen or halogen atom, or a nitro, methoxy or methylenedioxy group; $m$ is an integer of 1 to 2; and $n$ is an integer of 1 to 3) and the preparation thereof.

SUMMARY OF THE INVENTION

The oximino-phosphorothiolates of the formula (I) have such an insecticidal activity that enables the complete and advantageous controlling of agricultural and sanitary pests.

Referring now to the insecticidal activity in more detail, the present compounds have an excellent activity for killing not only harmful insects to rice plants such as rice stem borers, planthoppers, and leafhoppers, Lepidoptera insects harmful to fruits and vegetables, and sanitary insects such as flies, mosquitoes and gnats, but also other insects belonging to Lepidoptera, Diptera, Hemiptera and Coreoptera.

Furthermore, the present compounds exhibit so much a strong insecticidal activity against mites, Beetles such as azuki bean weevils and rice weevils, and plant-parasitic nematodes that they can widely be used for the simultaneous controlling of various species of insect by any application method of dusting, spraying and soil treatment.

In addition to the insecticidal activity, the present compounds have a herbicidal and a fungicidal activity at the same time. Since the present compounds exhibit so much a strong herbicidal activity against many species of weed that they can be said to have a wide range of application.

Furthermore, the present compounds are active against various plant diseases so much that they can be said to be a fungicide of a high controlling effect.

The preferred range of the present compounds is an oximino-phosphorothiolate of the formula,

wherein $R_1'$ is a methyl group; $R_2'$ is a methyl, ethyl, cycloalkyl($C_3$-$C_6$), ethoxymethyl, ethylthiomethyl, 2-methyl-1-propenyl or chloroethyl group; $R_3'$ is a methyl or ethyl group; and $R_4'$ is an alkyl($C_1$-$C_3$), propargyl, allyl, 2-bromo-2-propenyl, ethoxycarbonylmethyl, methylthioethyl, ethoxyethyl, N-methylamidomethyl, N,N-diallylamidomethyl, N,N-diethylamidomethyl, benzyl, (mono- or di-)methoxybenzyl, chlorobenzyl, nitrobenzyl, methylenedioxybenzyl, phenethyl, α-ethoxycarbonylbenzyl or 2-methylpiperidomethyl group.

The present compounds can be formulated into any preparation form of emulsifiable concentrates (containing 5 – 80% by weight of an active ingredient), wettable powders (containing 10 – 60% by weight of an active ingredient), oil sprays (containing 2 – 99% by weight of an active ingredient), dusts (containing 1 – 15% by weight of an active ingredient), granules (containing 1 – 15% by weight of an active ingredient), fine granules (containing 1 – 10% by weight of an active ingredient), coatings (containing 1 – 10% by weight of an active ingredient) and baits (containing 1 – 10% by weight of an active ingredient), according to the preparation of common organic phosphorus insecticides well known to the skilled in the art, and therefore can be applied in any preparation form according to application methods.

Referring now to the preparation of the present compounds of the formula (I), the compounds can be prepared, (A) by reacting an alkali metal salt of an oximino-phosphorothiolate of the formula (II),

wherein $R_1$, $R_2$ and $R_3$ are as defined above, and M is an alkali metal atom, with a halogenated compound of the formula (III), $$R_4 X \qquad (III)$$

wherein $R_4$ is as defined above and X is a halogen atom, or (B) by reacting an O,S-alkylphosphoryl chloride of the formula (IV),

wherein $R_3$ is as defined above, and $R_9$ is an alkyl or alkoxyalkyl group, with an oxime of the formula (V),

wherein $R_1$ and $R_2$ are as defined above, to prepare an oximino-phosphorothiolate of the formula (I'),

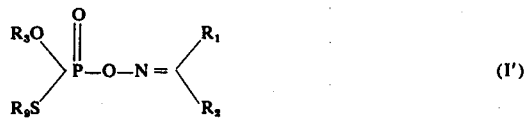

wherein $R_1$, $R_2$, $R_3$ and $R_9$ are as defined above.

In the process (A), solvents used are ketones and alcohols among which acetone, methanol and ethanol are preferred. Referring to the reaction conditions, alkali metal salts of the oximino-phosphorothiolate (II) are dissolved in the solvents described above, and then the halogenated compounds (III) are added thereto. The reaction temperature and time vary with the kind of alkali metal salts of the oximino-phosphorothiolate (II), however, temperatures of 0° to 80°C and times of ½ to 5 hours are sufficient. After the completion of reaction, the reaction mixture is freed of solvent after the removal of a precipitated salt by filtration, or as it is. The residue is extracted with a suitable organic solvent and the extract is washed with a dilute acid, dilute alkali and then water. The removal of the solvent gives the aimed product (I) in a high yield.

The alkali metal salts of the oximino-phosphorothiolate (II) used herein can easily be prepared by reacting an oximino-phosphorothioate of the formula (VI),

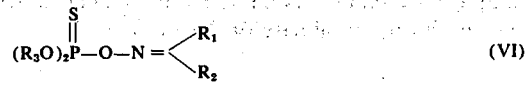

wherein $R_1$, $R_2$ and $R_3$ are as defined above, with an alkali hydrogen sulfide or an alkali metal salt of dithiocarbamic acid such as potassium N,N-dimethyldithiocarbamate in a suitable organic solvent.

DETAILED DESCRIPTION OF THE INVENTION

As examples of an alkali metal salt of the oximino-phosphorothioate (II), there are indicated the following compounds which are only given for the purpose of illustration and not to be interpreted as limiting.

potassium O-methyl-O-acetoximino phosphorothioate
potassium O-ethyl-O-acetoximino phosphorothioate
potassium O-methyl-O-(ethylmethylketoximino)phosphorothioate
potassium O-ethyl-O-(ethylmethylketoximino)phosphorothioate
sodium O-methyl-O-acetoximino phosphorothioate
potassium O-methyl-O-(methylethylthiomethylketoximino)-phosphorothioate
potassium O-methyl-O-(methylethoxymethylketoximino)-phosphorothioate
potassium O-methyl-O-(methyl-2-chloroethylketoximino)-phosphorothioate In the process (B), the reaction can easily be carried out by condensing an oxime of the formula (V) with the O,S-alkylphosphoryl chloride of the formula (IV) under acid-formation, in a suitable organic inert solvent and in the presence of an acid-binding agent, for example, organic bases such as triethylamine and pyridine, or inorganic bases such as sodium cabonate and caustic soda. The reaction temperature and time vary with the kinds of the solvent and acid-binding agent, however, temperatures of 0° to 110°C and times of ¼ to several hours are sufficient. After the completion of reaction, the aimed products can be obtained in a high yield by common after-treatments.

Some typical examples of the oximino-phosphorothiolate of the present invention will be exemplified as follows.

| Compound No. | Structure | Physical property |
|---|---|---|
| 1 | $\begin{array}{c}CH_3\\CH_3\end{array}\!\!>=NO-\overset{O}{\underset{SCH_3}{P}}-OCH_3$ | $n_D^{28.0} = 1.4752$ |
| 2 | $\begin{array}{c}CH_3\\CH_3\end{array}\!\!>=NO-\overset{O}{\underset{SCH_2-\langle H\rangle}{P}}-OCH_3$ | $n_D^{28.0} = 1.5359$ |
| 3 | $\begin{array}{c}CH_3\\CH_3\end{array}\!\!>=NO-\overset{O}{\underset{SCH_3}{P}}-OC_2H_5$ | $n_D^{28.0} = 1.5092$ |

| Compound No. | Structure | Physical property |
|---|---|---|
| 4 | CH₃\>N—O—P(=O)(OC₂H₅)(SCH₂C≡CH) / CH₃ | $n_D^{28} = 1.5036$ |
| 5 | CH₃\>N—O—P(=O)(OCH₃)(SCH₂C≡CH) / CH₃ | $n_D^{28.0} = 1.5006$ |
| 6 | CH₃\>N—O—P(=O)(OCH₃)(SCH₂C(Br)=CH₂) / CH₃ | $n_D^{25.0} = 1.5223$ |
| 7 | CH₃\>N—O—P(=O)(OCH₃)(SCH₂CH=CH₂) / CH₃ | $n_D^{28.0} = 1.4829$ |
| 8 | CH₃\>N—O—P(=O)(OCH₃)(SCH(C₆H₅)COOC₂H₅) / CH₃ | $n_D^{30} = 1.5163$ |
| 9 | CH₃\>N—O—P(=O)(OCH₃)(SCH₂COOC₂H₅) / CH₃ | $n_D^{30} = 1.5328$ |
| 10 | CH₃\>N—O—P(=O)(OCH₃)(SCH₂C(=O)N(cyclohexyl-CH₃)) / CH₃ | $n_D^{30} = 1.5082$ |
| 11 | C₂H₅\>N—O—P(=O)(OCH₃)(SCH₂—C₆H₅) / CH₃ | $n_D^{25.0} = 1.5320$ |
| 12 | CH₃\>N—O—P(=O)(OCH₃)(SCH₂CH₂SCH₃) / CH₃ | $n_D^{25.0} = 1.5118$ |
| 13 | (cyclopropyl)(CH₃)C=N—O—P(=O)(OC₂H₅)(SC₃H₇—(n)) | $n_D^{20.0} = 1.5110$ |
| 14 | CH₃\>N—O—P(=O)(OC₂H₅)(SCH₂—C₆H₄—OCH₃) / CH₃ | $n_D^{20.0} = 1.5433$ |
| 15 | C₂H₅OCH₂\>N—O—P(=O)(OCH₃)(SCH₃) / CH₃ | $n_D^{23} = 1.5356$ |
| 16 | C₂H₅SCH₂\>N—O—P(=O)(OC₂H₅)(SC₃H₇—(n)) / CH₃ | $n_D^{28} = 1.5138$ |
| 17 | (cyclohexyl)(H)C=N—O—P(=O)(OC₂H₅)(SC₃H₇—(n)) | $n_D^{26} = 1.5562$ |

| Compound No. | Structure | Physical property |
|---|---|---|
| 18 | $(CH_3)(CH_3)C=N-O-P(=O)(SC_3H_7-(n))(OC_2H_5)$ with CH(CH_3) group (H, CH_3) | $n_D^{26.0} = 1.5364$ |
| 19 | $(ClCH_2CH_2)(CH_3)C=N-O-P(=O)(SC_3H_7-(n))(OC_2H_5)$ | $n_D^{25} = 1.5333$ |
| 20 | $(CH_3)_2C=N-O-P(=O)(SCH_2-C_6H_4-Cl)(OCH_3)$ | $n_D^{22} = 1.5638$ |
| 21 | $(CH_3)_2C=N-O-P(=O)(SCH_2CH_2-C_6H_5)(OCH_3)$ | $n_D^{23} = 1.5722$ |
| 22 | $(CH_3)_2C=N-O-P(=O)(SCH_2-C_6H_4-NO_2)(OCH_3)$ | $n_D^{23} = 1.5665$ |
| 23 | $(CH_3)_2C=N-O-P(=O)(SCH_2-\text{methylenedioxyphenyl})(OCH_3)$ | $n_D^{26} = 1.5445$ |
| 24 | $(CH_3)_2C=N-O-P(=O)(SCH_2CH_2OC_2H_5)(OCH_3)$ | $n_D^{26} = 1.5440$ |
| 25 | $(CH_3)_2C=N-O-P(=O)(SCH_2C(=O)NHCH_3)(OCH_3)$ | $n_D^{20} = 1.5135$ |
| 26 | $(CH_3)_2C=N-O-P(=O)(SCH_2C(=O)N(CH_2HC=CH_2)_2)(OCH_3)$ | $n_D^{22} = 1.5226$ |
| 27 | $(CH_3)_2C=N-O-P(=O)(SCH_2C(=O)N(C_2H_5)_2)(OCH_3)$ | $n_D^{22} = 1.5326$ |
| 28 | $(CH_3)_2C=N-O-P(=O)(SCH_2-C_6H_3(OCH_3)_2)(OCH_3)$ | $n_D^{22} = 1.5535$ |

The present invention will be illustrated with reference to the following preparation examples.

PREPARATION 1 (Emulsifiable concentrates)

Each compound in the following Table was mixed with a solvent and an emulsifier in a proportion shown therein and in a proper order. Two homogeneous emulsifiable concentrates were thus obtained. In a practical application, the concentrates are diluted with water.

| Active ingredient (%) | | Solvent (%) | | Emulsifier (%) | |
|---|---|---|---|---|---|
| Compound No. 2 | 50 | Xylene | 30 | Sorpol 2020[(1)] | 20 |
| Compound No. 12 | 20 | Cyclohexanone | 50 | Sorpol 2492 | 30 |

Note: [(1)]A registered trademark of an emulsifier of Toho Kagaku Co., Ltd.

PREPARATION 2 (Wettable powders)

40 parts of Compound No. 5 and 5 parts of Sorpol 5029 (a registered trademark of Toho Kagaku Co., Ltd.) were thoroughly mixed. The mixed solution was added dropwise to 55 parts of 200 mesh talc while stirring well in a mortar to obtain a wettable powder. In a practical application, the wettable powder is diluted with water.

PREPARATION 3 (Dusts)

Each compound in the following Table was dissolved in a small amount of acetone and thoroughly mixed with 200 mesh talc in a proportion shown therein. Then acetone was removed by evaporation to give a dust. In a practical application, the dusts are applied as they are.

| Active ingredient | (%) | Diluent | (%) |
|---|---|---|---|
| Compound No. 8 | 2 | talc | 98 |
| Compound No. 20 | 4 | talc | 96 |

PREPARATION 4 (Granules)

Each compound, a binder and a diluent in the following Table were mixed well in this order and in a proportion as shown therein. Then each mixture was pasted with a small amount of water, granulated by a granulator and dried to give granules. In a practical application, the granules are dusted as they are.

| Active ingredient (%) | Binder (%) | Diluent (%) |
|---|---|---|
| Compound No. 1   2 | sodium lignosulfonate 1 | clay 97 |
| Compound No. 17  5 | sodium lignosulfonate 2 | clay 93 |

The present invention will be illustrated in more detail with reference to the following examples, which are only given for the purpose of illustration and not to be interpreted as limiting.

EXAMPLE 1 (Preparation of Compound No. 1)

0.1 mol of potassium O-methyl-O-acetoximino phosphorothioate was dissolved in 50 ml of methanol, and 0.11 mol of methyl iodide was added thereto at 20° to 30°C while stirring. The reaction mixture was stirred at the same temperature for 30 minutes and then methanol was distilled off therefrom. The remainder was extracted with 50 ml of chloroform, and then the extract was washed with a dilute alkali and water. Chloroform was removed by distillation to give brown, oily O-methyl-S-methyl-O-acetoximino phosphorothiolate ($n_D^{28.0}$ 1.4752) in a yield of 83%.

| | Calculated | Found |
|---|---|---|
| Phosphorus content | 15.70 % | 15.49 % |

EXAMPLE 2 (Preparation of Compound No. 13)

0.1 mol of cyclopropylmethylketoxime was dissolved in 70 ml of ether, and 0.1 mol of triethylamine was added thereto. 0.1 mol of O-ethyl-S-n-propylphosphoryl chloride was added dropwise at 5° to 10°C to the resulting solution which was stirred under cooling in ice. The reaction mixture was stirred at room temperature for several hours. After the reaction was completed, 50 ml of ice water were added thereto and the separated ether layer was washed with a dilute alkali and then a dilute acid. Thereafter ether was removed by distillation to give yellow, oily O-ethyl-S-n-propyl-O-cyclopropylmethylketoximino phosphorothiolate ($n_D^{20.0}$ 1.5110) in a yield of 89%.

| | Calculated | Found |
|---|---|---|
| Phosphorus content | 11.67 % | 11.82 % |

EXAMPLE 3 (Preparation of Compound No. 7)

O-methyl-S-allyl-O-acetoximino phosphorothiolate ($n_D^{25.0}$ 1.4829) was obtained in the same manner as described in Example 1.

| | Calculated | Found |
|---|---|---|
| Phosphorus content | 13.87 % | 13.72 % |

EXAMPLE 4 (Preparation of Compound No. 5)

O-methyl-S-propargyl-O-acetoximino phosphorothiolate ($n_D^{28.0}$ 1.5006) was obtained in the same manner as described in Example 1.

| | Calculated | Found |
|---|---|---|
| Phosphorus content | 14.00 % | 14.14 % |

EXAMPLE 5 (Preparation of Compound No. 6)

O-methyl-S-2-bromoallyl-O-acetoximino phosphorothiolate ($n_D^{25.0}$ 1.5223) was obtained in the same manner as described in Example 1.

| | Calculated | Found |
|---|---|---|
| Phosphorus content | 10.25 % | 10.27 % |

EXAMPLE 6 (Preparation of Compound No. 11)

O-methyl-S-benzyl-O-ethylmethylketoximino phosphorothiolate ($n_D^{25.0}$ 1.5320) was obtained in the same manner as described in Example 1.

| | Calculated | Found |
|---|---|---|
| Phosphorus content | 10.78 % | 11.46 % |

EXAMPLE 7 (Preparation of Compound No. 12)

O-methyl-S-2-methylthioethyl-O-acetoximino phosphorothiolate ($n_D^{26.0}$ 1.5118) was obtained in the same manner as described in Example 1.

| | Calculated | Found |
|---|---|---|
| Phosphorus content | 12.08 % | 11.80 % |

EXAMPLE 8 (Preparation of Compound No. 8)

0.1 mol of potassium O-methyl-O-acetoximino phosphorothioate was dissolved in 50 ml of methanol, and 0.1 mol of ethyl-α-bromo-α-phenylacetate was added thereto. Then the resulting solution was refluxed for 3 hours. After the reaction was completed, methanol was removed by distillation and then the procedure was carried out in the same manner as described in Example 1 to give O-ethyl-S-α-phenylethoxycarbonylmethyl-O-acetoximino phosphorothiolate ($n_D^{30}$ 1.5163).

|  | Calculated | Found |
|---|---|---|
| Phosphorus content | 8.97 % | 8.85 % |

EXAMPLE 9 (Preparation of Compound No. 10)

O-methyl-S-α-piperidinocarbamoylmethyl-O-acetoximino phosphorothiolate ($n_D^{30}$ 1.5082) was obtained in the same manner as described in Example 8.

|  | Calculated | Found |
|---|---|---|
| Phosphorus content | 9.61 % | 9.53 % |

EXAMPLE 10 (Effect on mosquito larvae)

The emulsifiable concentrates of the present compounds were each diluted to a required concentration with pure water. 200 ml of the aqueous solution were placed in a 300 ml beaker and 30 larvae of northern house mosquito (Culex pipens pullens) were released therein. The dead and alive after 24 hours were counted to calculate the mortality, and then values of $LC_{50}$ were obtained therefrom. The results are as shown in Table 1.

Table 1

| Compound No. | $LC_{50}$ (Active ingredient concentration) ppm |
|---|---|
| (4) | 0.24 |
| (5) | 0.11 |
| (6) | 0.34 |
| (8) | 0.076 |
| (9) | 0.49 |
| (12) | 0.14 |
| (19) | 0.16 |
| (22) | 0.12 |

EXAMPLE 11

Lethal effect on smaller brown planthoppers (Laodelphax striatellus)

Rice plants (15 to 20 cm tall) which had elapsed 15 days after germination were dipped for 1 minute into each aqueous dilute solution of the present compounds in a form of emulsifiable concentrates, and, after drying, placed in a large glass tube. Thereafter, 20 to 30 adults of planthoppers were released therein and covered with a wire net. The death and alive after 24 hours were counted to calculate the mortality, and then values of $LC_{50}$ were obtained therefrom. The results are as shown in Table 2.

Table 2

| Compound No. | $LC_{50}$ (Active ingredient concentration) ppm |
|---|---|
| (5) | 7.5 |
| (12) | 7.7 |
| (18) | 10.3 |

Table 2-continued

| Compound No. | $LC_{50}$ (Active ingredient concentration) ppm |
|---|---|
| (22) | 9.6 |

EXAMPLE 12

Effect on smaller brown planthoppers (Laodelphax striatellus) in the soil treatment Each 6% granule of the present compounds was applied in a proportion of 6 Kg/10 ares near the root of rice plants which had been grown up to the tillering stage in a 1/100,000 Wagner's pot. After 3 days, 30 adults of planthoppers were released and covered with a wire cage. After 24 hours, the death and alive were observed to calculate the mortality. The results are as shown in Table 3.

Table 3

| Compound No. | Mortality (%) |
|---|---|
| 5 | 83.3 |
| 7 | 75.0 |
| 8 | 71.6 |
| 12 | 89.2 |
| 15 | 73.6 |
| 22 | 75.5 |

EXAMPLE 13

Residual effect on smaller brown planthoppers (Laodelphax striatellus)

From 18 to 23 rice plants were grown up to a 3–4 - leaf stage in a flower pot of 10 cm in diameter, then a 1,000-fold aqueous dilute solution of each 50% emulsifiable concentrate of the present compounds was applied thereto. After air-drying, each pot was covered with a wire cage and 20 to 30 adults of planthoppers were released therein. The dead and alive after 24 hours were counted to calculate the mortality. Then, the same test was carried out two more times. The residual effects of the present compounds were checked from the mortalities thus obtained. The results are as shown in Table 4.

Table 4

| Compound No. | Mortality (%) | | |
|---|---|---|---|
|  | after 1 day | after 3 days | after 6 days |
| 2 | 100 | 60.6 | 48.4 |
| 8 | 100 | 75.1 | 53.6 |
| 10 | 100 | 73.6 | 55.1 |
| 12 | 100 | 90.3 | 77.8 |
| 14 | 100 | 62.8 | 49.3 |
| 22 | 100 | 70.0 | 50.1 |
| Meobal* | 100 | 31.4 | 12.3 |

Note: *Control, a registered trademark for 3,4-dimethyl-phenyl-N-carbamate of Sumitomo Chemical Co., Ltd.

EXAMPLE 14

Knock-down effect on green rice leafhoppers (Nephotettix cincpriceps)

Each 5% dust of the present compounds was dusted on potted rice plants which had elapsed 40 days after germination, in a proportion of 3 Kg/10 ares by means of a Bell jar duster. Thereafter about 30 green rice leafhopper adults (Nephotettix cincpriceps) were released and the whole was covered with a glass cylinder. The number of knocked down insects were counted from the outside at definite time intervals. The results are as shown in Table 5.

Table 5

| Compound No. | Knock-down ratio (%) | | | | | | KT$_{50}$ (min) |
|---|---|---|---|---|---|---|---|
| | $_5$min | $_{10}$min | $_{20}$min | $_{40}$min | $_{60}$min | $_{100}$min | |
| (8) | 44.8 | 55.2 | 56.0 | 72.4 | 79.0 | 82.8 | 14 |
| (9) | 24.1 | 34.5 | 59.3 | 69.0 | 93.1 | 96.6 | 17 |
| (12) | 10.0 | 16.7 | 60.0 | 76.7 | 90.0 | 96.7 | 18 |
| (20) | 15.0 | 40.3 | 58.6 | 67.3 | 83.7 | 90.0 | 16 |
| Meobal* | 3.0 | 8.0 | 44.5 | 69.6 | 81.3 | 91.5 | 23 |

Note:
*Same as above.

EXAMPLE 15

Lethal effect on carmine mite (*Tetranychus telarius*)

A large number of carmine mite adults were made parasitic on leaves of potted kidney beans at a 2-leaf stage which had elapsed 10 days after sowing. The leaves of kidney bean on which the carmine mites had been made parasitic were dipped for 1 minute in each aqueous solution of the present compounds in a form of wettable powder. Water was given to the leaves not to kill them, and after 48 hours the death and alive were observed microscopically to calculate the mortality. Values of LC$_{50}$ were obtained from the mortality. The results are as shown in Table 6.

Table 6

| Compound No. | LC$_{50}$ (Active ingredient concentration) ppm |
|---|---|
| (5) | 8.7 |
| (7) | 11.2 |
| (12) | 5.3 |
| (23) | 10.1 |

EXAMPLE 16

Acaricidal activity on carmine mites (*Tetranychus telarius*)

Carmine mite females were made parasitic on leaves of the potted kidney bean (2-leaf stage) which had elapsed 9 days after sowing, in a proportion of 10–15-/leaf, and bred at 27°C for a week in a constant temperature room. Then numerous carmine mites were found to be bred at various growth stages. At this time, an aqueous dilute solution of each wettable powder of the present compounds was sprayed in a proportion of 10 cc/pot by means of a turn table. After 10 days the degree of damage of kidney bean and the degree of breeding of carmine mite were observed and classified into five grades (−, +, ++, +++, ++++). The results are as shown in Table 7.

The degree of damage of kidney bean leaves:
−; damage is hardly observed,
++++; leaves ae dead,
and the degree of damage inbetween the two extremes was classified into three grades.
The degree of breeding of carmine mites;
−; the alive are less than 10,
++++; the alive are numerous,
and the degree of breeding inbetween the two extremes was classified into three grades.

Table 7

| Compound No. | Degree of damage | Degree of breeding |
|---|---|---|
| (2) | − | − |
| (5) | − | − ~ + |

Table 7-continued

| Compound No. | Degree of damage | Degree of breeding |
|---|---|---|
| (12) | − | − |
| (22) | − | − ~ + |

EXAMPLE 17

Lethal effect on rice stem borer (*Chilo suppressalis*)

Eggs just before hatch of rice stem borer were applied, in a proportion of 100/pot, near the root of rice plants which had been grown up to the tillering stage in an 1/100,000 Wagner's pot. After eggs were hatched and the larvae entered into stems of rice plants, a 1,000-fold aqueous dilute solution of each 50% emulsifiable concentrate of the present compounds was applied by means of a turn table. The dead and alive were observed to calculate the mortality 4 days after application. The results are as shown in Table 8.

Table 8

| Compound No. | Mortality (%) |
|---|---|
| (5) | 98.9 |
| (12) | 100 |
| (18) | 73.6 |
| (22) | 80.1 |

EXAMPLE 18

Effect on nematode 0.5 ml of a nematode-containing aqueous solution separated from food according to Baermann's Method was placed in a beaker with ground stopper containing 0.5 ml of an aqueous dilute solution of each emulsifiable concentrate of the present compounds. The concentration of an active ingredient in the mixture was adjusted to a required value. After 24 hours the death and alive were observed microscopically to calculate the mortality. The results are as shown in Table 9.

Table 9

| Compound No. | Concentration (ppm) | Mortality (%) |
|---|---|---|
| (1) | 500 | 100 |
| (4) | 500 | 100 |
| (8) | 500 | 98.7 |
| (11) | 500 | 100 |
| (13) | 500 | 100 |
| (14) | 500 | 100 |
| (17) | 500 | 100 |
| (21) | 500 | 100 |
| (24) | 500 | 97.3 |
| D-D* | 500 | 85.0 |

Note: *Control, 1,3-dichloropropene

EXAMPLE 19

Pre-emergence application

Seeds of barnyard grass (*Echinochloa crus-galli*) and large crabgrass (*Digitaria sanquinalis*) as representatives of grassy weeds and those of raddish, redroot pigweed (*Amaranthus retroflexus*), common purslane (*Portulaca oleracea*) and common lambsquarter (*Chenopodium album*) as representatives of broadleaved weeds were individually sowed in flower pots of about 10 cm in diameter. After covering the seeds with soil, test compounds as shown in Table 10 were individually applied to the soil treatment. Thereafter the plants were grown in a green house and 20 days after application the herbicidal effects of the compounds were observed, the results of which are as shown in Table 10.

The herbicidal effects were evaluated by the numerals ranging from 0 (not damaged) to 5 (completely killed). All the test compounds were used in the form of wettable powder and diluted with water before application.

Table 10

| Compound No. | Amount applied (g/a) | Barnyard grass | Large crabgrass | Raddish | Redroot pigweed | Common purslane | Common lambsquarter |
|---|---|---|---|---|---|---|---|
| (2) | 200 | 4 | 4 | 0 | 4 | 4 | 4 |
|  | 100 | 3 | 3 | 0 | 3 | 3 | 3 |
| (8) | 200 | 4 | 4 | 0 | 4 | 3 | 3 |
|  | 100 | 4 | 4 | 0 | 3 | 3 | 3 |
|  | 200 | 5 | 5 | 0 | 5 | 5 | 4 |
| (10) | 100 | 5 | 5 | 0 | 4 | 4 | 4 |
|  | 50 | 5 | 5 | 0 | 3 | 3 | 3 |
| Penta-* chloro phenol | 100 | 3 | 4 | 4 | 4 | 4 | 4 |

Note: *Control

EXAMPLE 20

Herbicidal effects and phytotoxicity tests

Wagner pots of 14 cm in diameter, which had been packed with 1.5 Kg of paddy field soil, were brought into the state of paddy fields. To the pots were transplanted rice seedlings at a 3- leaf stage. Further, seeds of barnyard grass (*Echinochloa crus-galli*) were sowed in the pots and a required amount of test compounds were individually applied to the soil under water lodged condition. 25 days after application, the degrees of herbicidal activity and phytotoxicity were checked on the above-described plants which had been transplanted or sowed, and on broad-leaved weeds, e.g., monochoria (*Monochoria viaginalis Presl.*), false pimpernel (*Linderna Pyxidaria*) and toothcup (*Rotala indica Koehne*), which had been spontaneously germinated. The test compounds were used in the form of wettable powder. The results obtained are as shown in Table 11. The herbicidal effect and the phytotoxicity were evaluated as follows by the numerals ranging from 0 to 5.

| Effect on plants | |
|---|---|
| 0 | no effect |
| 1 | very slightly affected |
| 2 | slightly affected |
| 3 | moderately affected |
| 4 | considerably affected |
| 5 | completely killed |

Table 11

| Compound No. | Amount applied (g/a) | Herbicidal effects | | Phytotoxicity on rice plants |
|---|---|---|---|---|
|  |  | Barnyard grass | Broad-leaved weeds |  |
| (2) | 50 | 5 | 5 | 0 |
|  | 25 | 3 | 4 | 0 |
| (8) | 50 | 5 | 5 | 0 |
|  | 25 | 5 | 5 | 0 |
| (9) | 50 | 5 | 5 | 0 |
|  | 25 | 3 | 3 | 0 |
| (10) | 50 | 5 | 5 | 1 |

Table 11-continued

| Compound No. | Amount applied (g/a) | Herbicidal effects | | Phytotoxicity on rice plants |
|---|---|---|---|---|
|  |  | Barnyard grass | Broad-leaved weeds |  |
|  | 25 | 5 | 5 | 0 |
|  | 100 | 5 | 5 | 3 |
| Pentachloro-phenol * | 50 | 4 | 5 | 2 |

Note: * Control

EXAMPLE 21

Protective activity on rice blast (*Piricularia oryzae*)

On the rice plants (variety: Kinki No. 33 ) which had been grown up to a 4-leaf stage in a flower pot of 9 cm in diameter, was dusted each dust of the present compounds in a proportion of 3 Kg/10 ares by means of a Bell jar duster. After 1 day, a spore suspension of rice blast fungus (*Piricularia oryzae*) was inoculated by spraying, and after 5 more days the number of spot produced on leaves was counted to check the protective activity.

As is clear from the test results shown in Table 12, the present compounds have a higher protective activity than that of the control compound.

Table 12

| Compound No. | Concentration | Control of disease |
|---|---|---|
| (2) | 3 Kg/10 ares | 97 |
| (11) | " | 95 |
| (14) | " | 100 |
| (20) | " | 93 |
| (21) | " | 99 |
| * O,O-diethyl-S-benzyl-phosphorothiolate | " | 80 |

Note: * Control

EXAMPLE 22

Protective activity on damping off disease of cucumber (*Pellicularia filamentosa*)

A flower pot of 9 cm in diameter was packed with field soil on which 10 ml of infested soil containing cultured *Pellicularia filamentosa* were spread uniformly. Then an aqueous solution of each emulsifiable concentrate of the present compounds was applied in a proportion of 10 ml/pot. After three days, 10 seeds of cucumber (variety: Kaga Aonaga-fushinari) were sowed in each pot, and after 5 more days the disease severity was checked. A percentage of healthy seedlings was calculated according to the following formula.

Percentage of healthy seedlings =

$$\frac{\text{number of healthy seedlings in each treated plot}}{\text{number of germination in an untreated and uninoculated plot}} \times 100$$

The test results are as shown in Table 13. It can clearly be shown that the present compounds have a higher protective activity than that of the control compound.

Table 13

| Compound No. | Concentration (ppm) | Percentage of healthy seedlings (%) |
|---|---|---|
| (4) | 1,000 | 95 |
| (7) | 1,000 | 90 |
| PCNB* | 1,000 | 85 |

Note:
*Control, pentachloronitrobenzene

While the invention has been described in detail and with reference to specific embodiments thereof, it will be apparent to one skilled in the art that various changes and modifications can be made therein without departing from the spirit and scope thereof.

What is claimed is:

1. An oximino-phosphorothiolate of the formula,

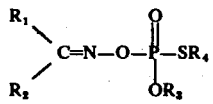

wherein $R_1$ is a $C_1$–$C_4$ alkyl group; $R_2$ is a $C_1$–$C_4$ alkyl group; $R_3$ is a $C_1$–$C_4$ alkyl group and $R_4$ is an alkyl thioalkyl group wherein each alkyl moiety thereof has 1 to 4 carbon atoms or an alkoxy alkyl group wherein the alkoxy moiety and the alkyl moiety thereof have 1 to 4 carbon atoms.

2. An oximino-phosphorothiolate of formula,

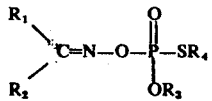

wherein $R_1$ is a $C_1$–$C_4$ alkyl group; $R_2$ is a $C_1$–$C_4$ alkyl group; $R_3$ is a $C_1$–$C_4$ alkyl group and $R_4$ is an alkyl thioalkyl group wherein each alkyl moiety thereof has 1 to 4 carbon atoms.

3. An oximino-phosphorothiolate of the formula,

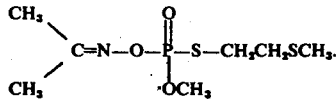

* * * * *